United States Patent [19]

Hochstrasser

[11] Patent Number: 4,950,708

[45] Date of Patent: Aug. 21, 1990

[54] STABLE POLYACRYLAMIDE GELS CONTAINING CHAOTROPIC AGENTS

[75] Inventor: Denis F. Hochstrasser, Geneva, Switzerland

[73] Assignee: Bio-Rad Laboratories, Inc., Hercules, Calif.

[21] Appl. No.: 237,819

[22] Filed: Aug. 29, 1988

[51] Int. Cl.$^5$ .................... C08K 5/20; C08F 271/02; C08F 265/10

[52] U.S. Cl. .................... 524/728; 524/808; 524/809; 524/813; 524/555; 525/279; 525/281; 525/296; 526/259

[58] Field of Search ............... 524/210, 211, 227, 720, 524/555, 729, 808; 525/281, 279, 296; 526/259

[56] References Cited

U.S. PATENT DOCUMENTS 4,548,869 10/1985 Ogawa et al. .................... 524/521

OTHER PUBLICATIONS

U.S. Dept. of Health & Human Services, No. PB88–212,758, 12 Jan. 88.

U.S. Dept. of Health & Human Services, No. PB 88–179,809, 24 Feb. 1988.

*Primary Examiner*—Joseph L. Schofer
*Assistant Examiner*—Mark D. Sweet
*Attorney, Agent, or Firm*—Townsend and Townsend

[57] ABSTRACT

Polyacrylamide gels containing chaotropic agents such as urea as solubilizing agents for protein or nucleic acid separations are rendered stable for prolonged periods of time by the use of certain diacrylyl compounds with tertiary amide groups as cross linking agents. These compounds have the general structure

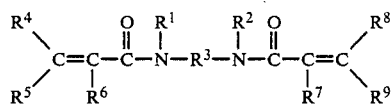

where the R groups are generally saturated hydrocarbon groups and $R^4$ through $R^9$ may also be hydrogen. When used as cross linkers, these compounds have the further advantage of preventing urea crystallization at lowered temperatures.

7 Claims, No Drawings

STABLE POLYACRYLAMIDE GELS CONTAINING CHAOTROPIC AGENTS

This invention relates to polyacrylamide gels used in electrophoresis, and in particular to polyacrylamide gels containing a chaotropic agent, such as urea, as a protein solubilizing agent.

BACKGROUND AND SUMMARY OF THE INVENTION

The inclusion of a chaotropic agent, such as urea, in both starch and acrylamide gels has permitted electrophoretic separation in these gels of certain classes of proteins or nucleic acids which would not otherwise be separated. Since chaotropic agents in high concentrations prevent the formation of hydrogen bonds, protein complexes or aggregates, the structure of which is maintained by such bonds, are readily disassociated in the presence of these agents. Separation may thus be achieved, for example, by diluting the sample mixture in a urea solution and separating it electrophoretically in a gel which contains urea. As is well known, protein complexes or aggregates or nucleic acids are readily disassociated in urea at room temperature without undergoing a change in charge. Urea-containing gels are thus highly useful in isoelectric focussing, both alone and at the first stage of two-dimensional electrophoresis.

It is known that polyacrylamide gels, formed from acrylamide monomers with the inclusion of bisacrylamide (N,N'-methylenebis(acrylamide)) as a cross linking agent with urea included as a solubilizer, must be used soon after they are formed. If such gels are stored more than 24 hours at room temperature, their ability to separate proteins deteriorates significantly. While refrigeration lessens the rate of deterioration, it gives rise to another problem, urea crystallization Such crystallization occurs, for example, in gels with 9M urea at 4° C. within a few hours.

The deterioration of the gels precludes precasting and storage for any appreciable period of time, and seriously detracts from the ease of using such gels. The need to prepare the gels within a few hours of their use not only limits the operator's efficiency, but also creates the possibility of variations from one gel to the next, introducing non-reproducibility, as well as increasing the likelihood of errors and lost time due to unusable data.

It has now been discovered that the problems of both gel deterioration and urea crystallization are eliminated by the use of diacrylyl compounds containing tertiary amide groups as cross linking agents. While the acrylyl moieties in the compounds provide the compatibility with the polyacrylamide chains which is characteristic of the bis-acrylamide cross linking agent, the tertiary structure of the nitrogens as opposed to their secondary structure in bis-acrylamide is unexpectedly found both to impart a long term stability to the gel and to function as an "anti-freezing" agent as well. The latter is particularly surprising in view of the ineffectiveness of certain additives known for their anti-freezing properties in other media.

DETAILED DESCRIPTION OF THE INVENTION AND PREFERRED EMBODIMENTS

The diacrylyl cross linking agents used in accordance with the present invention are those having the formula

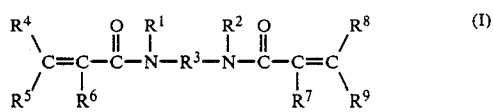

in which:

$R^1$, $R^2$ and $R^3$ are defined such that $R^1$ and $R^2$ are independently $C_1$-$C_5$ alkyl, and $R^3$ is $C_1$-$C_8$ alkylene; or $R^1$ and $R^2$ are joined to form $C_1$-$C_8$ alkylene, and $R^3$ is $C_1$-$C_8$ alkylene; or $R^1$ is joined to $R^3$ to form a saturated hydrocarbyl group of 3 to 10 carbon atoms which, together with the N atom to which $R^1$ and $R^3$ are joined, forms a N-containing ring, and $R^2$ is $C_1$-$C_5$ alkyl; or $R^1$ and $R^2$ are joined to $R^3$ to form a saturated hydrocarbyl group of 7 to 15 carbon atoms which together with the N atoms forms two N-containing rings; and $R^4$, $R^5$, $R^6$, $R^7$, $R^8$, and $R^9$ are independently selected from the group consisting of H and $C_1$-$C_5$ alkyl.

Within this formula, certain embodiments are preferred, notably those in which $R^1$ and $R^2$ are independently $C_1$-$C_5$ or $C_1$-$C_3$ alkyl or are joined to form $C_1$-$C_8$ or $C_2$-$C_4$ alkylene, and $R^3$ is $C_1$-$C_8$ or $C_1$-$C_4$ alkylene; and those in which $R^4$, $R^5$, $R^6$, $R^7$, $R^8$, and $R^9$ are independently H, $CH_3$, or $C_2H_5$.

Examples of compounds within the scope of Formula I are as follows:

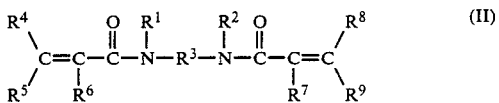

in which $R^1$ and $R^2$ are lower alkyls, $R^3$ is alkylene, and $R^4$ through $R^9$ are as defined above;

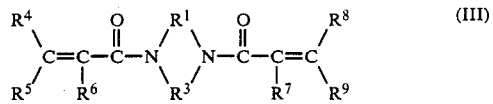

where $R^1$ and $R^3$ are lower alkylenes, and $R^4$ through $R^9$ are as defined above;

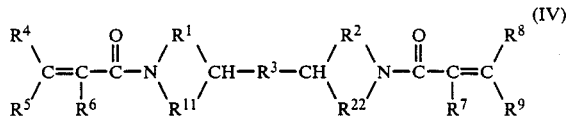

where $R^1$, $R^{11}$, $R^2$, $R^{22}$, and $R^3$ are lower alkylenes, and $R^4$ through $R^9$ are as defined above.

The term "alkyl" is used herein to denote a monovalent saturated hydrocarbon group, including both straightchain and branched-chain structures. Examples are methyl, ethyl, propyl, isopropyl, butyl, isobutyl, t-butyl, pentyl, hexyl, and 2-methylhexyl.

The term "alkylene" is used herein to denote a divalent saturated hydrocarbon group, including both straight-chain and branched-chain structures. Examples include —CH$_2$—, —CH$_2$—CH$_2$—, —CH$_2$—CH$_2$—CH$_2$—, —CH$_2$—C(CH$_3$)$_2$— and —CH$_2$—C(CH$_3$)$_2$—CH$_2$—.

The term "lower" when used to describe alkyl and alkylene groups refers to groups having one to four carbon atoms.

The term "hydrocarbyl" is used herein in a general sense to denote any group consisting solely of hydrogen and carbon atoms.

The cross linking agents used in the practice of the present invention may be prepared by conventional techniques which will be readily apparent to those skilled in the art. An appropriately substituted anhydrous diamine, for example, may be combined with triethylamine in a suitable solvent such as tetrahydrofuran (THF) with cooling, followed by the addition of an acryloyl chloride to produce a diamino-diacryloyl compound. The precipitated amine hydrochloride may be removed by filtration to leave a THF solution of the product.

Gel formation using the above-described cross linking agents is likewise done in accordance with conventional procedures. The selection of polymerization initiators, accelerators, operating conditions, concentrations of gel components, and ratio of acrylamide monomer to cross linking agent are well within the routine skill of those skilled in the gel electrophoresis art. In some cases, these parameters will be tailored to achieve gels of specific characteristics such as density and porosity, as well as gels designed for separating particular types of solutes.

In general, the parameters are not critical and may vary over wide ranges. The chaotropic agent will generally be present in an amount sufficient to solubilize the solutes being separated. The term "solute-solubilizing amount" is used herein to denote such an amount, the solute generally being proteins, protein complexes or aggregates, or nucleic acids. In most applications where urea is used, for example, gels containing urea in amounts ranging from about 8M to about 10M, will provide the best results. The same is true for gels in which the mole ratio of cross linking agent to acrylamide used for the polymerization ranges from about 0.001 to about 1.0, preferably from about 0.003 to about 0.03.

The following examples are offered for illustrative purposes, and are intended neither to limit nor define the invention in any manner.

The abbreviations used in these examples are as follows:
THF: Tetrahydrofuran
IEF: Isoelectric focusing
CHAPS: Cholamidopropyldimethylhydroxypropanesulfonate
TEMED: Tetramethylenediamine
DTE: Dithioerythritol
DTT: Dithiothreitol
SDS: Sodium dodecyl sulfate
Tris: Tris(hydroxymethyl)-aminomethane
PAGE: Polyacrylamide gel electrophoresis
All water used in the procedures was deionized water.

EXAMPLE 1

Preparation of Cross Linker

This example illustrates the preparation of a specific cross linking agent for use in accordance with the present invention.

Triethylamine (21 mmol) and diethylenediamine (piperazine) (10 mmol) were dissolved in 50 mL tetrahydrofuran. The resulting solution was cooled in an acetone/ice bath, and 20 mL of a THF solution containing 20 mmol acryloyl chloride was slowly added with constant stirring over 20 min. The reaction temperature was maintained at 0° C or below. When the acryloyl chloride addition was complete, the reaction vessel was removed from the cooling bath and permitted to equilibrate to room temperature for 15 min to allow the reaction to run to completion. Hydroquinone (6 mg) was then added to the reaction mixture, and the resulting mixture was filtered through a medium pore sintered glass filter. The precipitate was discarded and the filtrate was titrated to a pH of 7.0 with 5N HCl. The solution was then refiltered.

The product was then extracted from the solution by countercurrent distribution with petroleum ether. The product was then allowed to crystallize from the extract at 20° C. The crystals were collected by filtration through a sintered medium pore glass filter. The crystals were then redissolved in fresh THF, re-extracted with petroleum ether and crystallized as before.

The overall recovery was greater than 30%. The structure was verified as that of diacrylyl piperazine by proton NMR spectroscopy and melting point determination (92–94° C.).

EXAMPLE 2

Preparation of IEF Capillary Gels

This example demonstrates the preparation of urea-containing polyacrylamide gels cross linked in accordance with the present invention, using diacrylylpiperazine as the cross linking agent.

A solution was prepared by dissolving 9.5 g of urea in 6.5 mL of deionized water and 3.0 mL of an acrylamidediacrylylpiperazine stock solution, the latter formed by dissolving 30 g of acrylamide and 1.0 g of diacrylylpiperazine in water to a final volume of 100 mL. To the urea solution were added 0.8 mL of Bio-Lyte 3/10 and 0.2 mL of Bio-Lyte 5/7 ampholytes (Products of Bio-Rad Laboratories, Richmond, Calif.). Separately, a CHAPS solution was prepared by dissolving 0.4 g of CHAPS in 0.9 mL water. This CHAPS solution was then combined with the urea solution, and the final mixture degassed for 1 minute. To initiate polymerization, 20 μL of TEMED and 40 μL of a 100 g/L ammonium persulfate solution were added.

Glass capillary tubes (1.0 mm i.d. ×75 mm) and plastic capillary tubes having a square cross section (1.0 mm along each side) and the same length were placed in a 75×12 mm (i.d.) glass test tube. The above solution was pipetted into this glass test tube while avoiding air bubble formation, with the result that the capillary tubes became filled with the solution by capillary action. Polymerization was allowed to continue for 2 hours, after which time some of the capillary tubes were removed from the test tube, washed with water to remove excess acrylamide on the outsides of the tubes, and inserted into an IEF chamber for immediate use. The remaining capillary tubes were left in the test tube, which was covered with a plastic sheet and stored at room temperature for more than four weeks. Other capillaries similarly prepared were stored in a separate test tube at 4° C. for the same period of time, after which time no crystallization of the urea was observed These capillaries were then removed from the test tubes in the same manner as the others, and inserted into an IEF chamber for use.

EXAMPLE 3

Use in IEF Separations

In an Eppendorf tube, 5 μL of plasma and 10 μL of a denaturing solution made up from 1 g SDS and 0.232 g DTE or DTT in 10 mL water were combined and heated at 95° C. for 5 minutes, then permitted to cool at room temperature for 2 minutes. To the resulting solution were then added 500 μL of water and 485 μL of a solution consisting of 100 μg of DTE or DTT, 400 μg of CHAPS, 5.4 g of urea, 500 μL of BioLyte 3/10, and 6.5 mL of water. To load the capillary tubes containing the gels prepared in Example 1, 5 μL aliquots of the plasma sample in its final diluted form were loaded onto each capillary tube at one end through plastic connecting tubing.

The ends of the gels where samples had been loaded were then overlayered with a catholyte consisting of 20 mmol/L aqueous NaOH. An aqueous 6 mmol/L $H_3PO_4$ solution was used as the anolyte. Isoelectric focusing was performed on a Bio-Rad Mini-PROTEAN II Tube Cell, using a constant voltage of 200 V for 1 hour, followed by 500 V for 2 hours, and finally 1000 V for 1 hour.

EXAMPLE 4

Second-Dimension Separation and Staining

The gels containing the focused solute zones prepared in Example 3 were extruded from the capillary tubes with a tuberculin syringe connected to an extruding device filled with deionized water. The extruded gels were placed on a sheet of mylar and blotted gently to remove excess water. The gels were then rinsed with 50 μL of a transfer solution containing 8 mL of 0.5 g/L bromophenol blue solution, 40 mL of 100 g/L SDS solution, 20 mL of 0.5 mol/L Tris HCl buffer, pH 6.8, and 72 mL of deionized water.

To provide the focused zones with a second-dimension separation, slab SDS-PAGE gels were prepared with uniform acrylamide concentrations of 13.3% by weight. To prepare these gels, 16.5 mL of water were mixed with 14.5 mL of Tris HCl solution (1.5 mol/L with pH adjusted to 8.8 with HCl), 24 mL of an acrylamide-diacrylylpiperazine stock solution, the latter formed by dissolving 30 g of acrylamide and 0.8 g of diacrylylpiperazine in water to a final volume of 100 mL, and 0.4 mL of a 50 g/L aqueous sodium thiosulfate solution. The solution was degassed, and 0.6 mL of 100 g/L ammonium persulfate and 0.35 mL of dimethylpiperazine were added to initiate polymerization. The solution was poured between glass plates selected for use in a Bio-Rad Mini-PROTEAN II Electrophoresis Cell, overlayered with water-saturated secbutanol, and permitted to stand while polymerization took place, which was completed within 15 minutes. The tops of the resulting gels were washed with deionized water to remove any remaining sec-butanol.

The extruded tube gels containing the focused zones were inserted in the space between the glass plates above the slab gels, with full contact between the two and avoidance of air bubbles. Electrophoresis was then run, using an electrolyte buffer consisting of 1 g SDS, 6 g Tris base and 28.8 g glycine in 1 L deionized water, at 10 mAmp constant current per gel, for 3 hours. During the course of this time, the voltage increased from 60 V to 120 V.

The slab gels were then removed from the glass plates, washed with water for 5 minutes and soaked in a fixing solution consisting of 100 mL of ethanol/acetic acid/water (40/10/50) for 1 hour on an orbital shaker at 36 rpm. The fixing solution was then replaced with a solution of the same components at 5/5/90 proportions for 3 hours or more. The gels were then washed with water for 5 minutes and soaked in 100 mL/L glutaraldehyde solution for 30 min. The glutaraldehyde was then removed with seven water washes, and the gels were stained for 10 minutes in an ammoniacal $AgNO_3$ solution (6 g $AgNO_3$ dissolved in 30 mL water, then combined with a solution containing 160 mL water, 10 mL concentrated $NH_4OH$ and 1.5 mL of 10 mol/L NaOH, and diluted with water to a final volume of 750 mL) at 20° C., followed by a water wash. The image was then developed in a citric acid/formaldehyde solution (0.1 g and 1 mL, respectively in 1 L of water) until a slight background stain appeared. Development was then stopped with acetic acid/water (5/95) and the stained gels were stored in glycerol/ethanol/water (7/10/83).

Examination of the stained gels revealed well-defined stained regions corresponding to the proteins in the original plasma sample, indicating that the capillary gels were fully viable, even after 4 weeks of storage at both room temperature and 4° C. The stain patterns in the slab gels further indicated that those capillary gels used after 4 weeks of storage showed no significant difference over those used immediately after the gel was formed, confirming that the destructive effects of the urea on the polyacrylamide was dramatically diminished or completely eliminated by the use of diacrylylpiperazine as the cross linking agent.

EXAMPLE 5

Storage Studies

This example demonstrates the unusual ability of diacrylylpiperazine to suppress the crystallization of urea at low temperatures, and compares diacrylylpiperazine to freezing point depressants.

IEF capillary gels were prepared following the procedure of Example 2, together with similar gels using 7.5 g of urea rather than 10 g, as well as further gels identical to the first group in all respects except for the use of methylene-bisacrylamide as the cross linking agent in place of diacrylylpiperazine and in an equivalent amount. Still further gels were prepared with methylene-bisacrylamide as the cross linking agent and including (individually) 1 mL of 75% aqueous glycerol, 1 mL of 50% aqueous sucrose, and 1 g of diglycine anhydride as candidates for anti-crystallization agents. Gels of all types were stored under a variety of conditions: 4° C. for 24 hours, and -20° C. for 24 hours.

All of the cooled gels except for those cross linked with diacrylylpiperazine showed evidence of urea crystallization. Those cross linked with diacrylylpiperazine showed that the latter was effective in preventing urea crystallization at both urea levels.

The foregoing is offered primarily for purposes of illustration. It will be readily apparent to those skilled in the art that modifications, variations and alternatives may be substituted for the materials and procedures described above without departing from the spirit and scope of the invention.

What is claimed is:

1. A polyacrylamide electrophoresis gel containing urea in an amount ranging from about 8M to about 10M, and comprised of a polyacrylamide cross linked with a cross linking agent having the formula

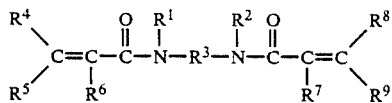

in which:

R$^1$, R$^2$ and R$^3$ are defined such that:

R$^1$ and R$^2$ are independently C$_1$–C$_3$ alkyl, and R$^3$ and C$_1$–C$_4$ alkylene; or R$^1$ and R$^2$ are joined to form C$_1$–C$_4$ alkylene, and R$^3$ is C$_1$–C$_4$ alkylene; or R$^1$ is joined to R$^3$ to form a saturated hydrocarbyl group of 3 to 10 carbon atoms which together with the N atoms to which R$^1$ and R$^3$ are joined forms a N-containing ring, and R$^2$ is C$_1$–C$_5$ alkyl; or R$^1$ and R$^2$ are joined to R$^3$ to form a saturated hydrocarbyl group of 7 to 15 carbon atoms which together with the N atoms forms two N-containing rings; and R$^4$, R$^5$, R$^6$, R$^7$, R$^8$ and R$^9$ are independently selected from the group consisting of H, CH$_3$ and C$_2$H$_5$.

2. A polyacrylamide electrophoresis gel in accordance with claim 1 in which R$^1$, R$^2$ and R$^3$ are defined such that R$^1$ and R$^2$ are independently C$_1$–C$_3$ alkyl or are joined to form C$_2$–C$_4$ alkylene; and R$^3$ is C$_1$–C$_4$ alkylene.

3. A polyacrylamide electrophoresis gel in accordance with claim 1 in which R$^1$ and R$^2$ are joined to form C$_2$–C$_4$ alkylene, R$^3$ is C$_1$–C$_4$ alkylene.

4. A polyacrylamide electrophoresis gel in accordance with claim 1 in which R$^1$ and R$^2$ are joined to form C$_2$–C$_4$ alkylene, R$^3$ is C$_1$–C$_4$ alkylene, and R$^4$, R$^5$, R$^6$, R$^7$, R$^8$, and R$^9$ are each H.

5. A polyacrylamide electrophoresis gel in accordance with claim 1 in which R$^1$ and R$^2$ are joined to form —CH$_2$—CH$_2$—, R$^3$ is —CH$_2$—CH$_2$—, and R$^4$, R$^5$, R$^6$, R$^7$, R$^8$, and R$^9$ are each H.

6. A polyacrylamide electrophoresis gel in accordance with claim 1 in which the mole ratio of cross linking agent to acrylamide in said polyacrylamide is from about 0.001 to about 1.0.

7. A polyacrylamide electrophoresis gel in accordance with claim 1 in which the mole ratio of cross linking agent to acrylamide in said polyacrylamide is from about 0.003 to about 0.03.

* * * * *